United States Patent [19]

Stockel

[11] Patent Number: 4,615,882

[45] Date of Patent: Oct. 7, 1986

[54] DISINFECTANT SOLUTION FOR CONTACT LENS

[76] Inventor: Richard F. Stockel, 475 Rolling Hills Rd., Bridgewater, N.J. 08807

[21] Appl. No.: 729,560

[22] Filed: May 2, 1985

Related U.S. Application Data

[63] Continuation-in-part of Ser. No. 424,197, Sep. 27, 1982, abandoned.

[51] Int. Cl.$^4$ .................... A61K 31/79; C11D 3/48; C08F 8/00; C08B 11/20
[52] U.S. Cl. .................... 424/80; 252/106; 252/351; 252/357; 424/78; 424/81; 514/63; 514/840; 525/102; 525/409; 525/431; 525/446; 536/87
[58] Field of Search ............ 424/78, 80, 81, 184; 525/102, 409, 431, 446; 536/87; 252/106, 351, 357

[56] References Cited

U.S. PATENT DOCUMENTS

| | | | |
|---|---|---|---|
| 3,624,120 | 11/1971 | Yetter | 424/184 |
| 3,639,576 | 2/1972 | Kaspar et al. | 424/78 |
| 3,730,701 | 5/1973 | Isquith et al. | 71/67 |
| 3,794,736 | 2/1974 | Abott et al. | 424/84 |
| 3,817,739 | 6/1974 | Abott et al. | 71/67 |
| 3,882,036 | 5/1975 | Krezanoski et al. | 424/329 |
| 3,954,644 | 5/1976 | Krezanoski et al. | 252/106 |
| 4,029,817 | 6/1977 | Blanco et al. | 424/80 |
| 4,046,706 | 9/1977 | Krezanoski | 252/106 |
| 4,394,378 | 7/1983 | Klein | 71/67 |

*Primary Examiner*—Douglas W. Robinson
*Attorney, Agent, or Firm*—Walter Katz

[57] ABSTRACT

An aqueous anti-microbial disinfectant solution for contact lenses contains an effective amount of an active ingredient which is an anti-microbial, organosilicon quaternary ammonium salt chemically bonded to a water soluble, high molecular weight organic polymer. The solution is non-toxic and non-irritating to the eye, and does not adsorb or penetrate into a contact lens.

37 Claims, No Drawings

DISINFECTANT SOLUTION FOR CONTACT LENS

CROSS-REFERENCE TO RELATED PATENT APPLICATIONS

This application is a continuation-in-part of my co-pending application Ser. No. 424,197, filed Sept. 27, 1982 now abandoned.

BACKGROUND OF THE INVENTION

Hydrophilic and partially hydrophilic plastic materials for use in the manufacture of contact lenses are extensively described in the literature. For example, U.S. Pat. Nos. Re. 27,401, 2,976,576; 3,499,862; 3,503,942; 3,361,858; 3,699,089 and 3,822,089 describe processes for producing three dimensional, sparingly crosslinked, polymeric materials and/or contact lenses of such materials. These materials have the extraordinary ability to absorb water with concomitant swelling to a soft mass. The resulting hydrogel material is characterized by good mechanical properties, complete transparency, high resistance to degradation in boiling water, inertness, good optical geometry and shape retention. Given the fact that wearers of soft contact lenses experience a comfort not heretofore obtained with hard contact lenses, i.e., poly (methyl methacrylate), it is small wonder that the soft contact lens industry has displayed remarkable growth during the 1970's, and forecasts indicate further vibrant growth for the 1980's.

However, one of the problems associated with soft contact lenses concerns sterilizing and cleaning them. The very property of soft lenses which permit them to absorb sizeable quantities of water, e.g., upwards of 38 weight percent water based on the total weight of the hydrogel, also allows preservatives which might otherwise be used for cleaning and sterilizing to be absorbed or even concentrated or later released when the soft contact lens is on the eye. This can have the harmful result of damaging or staining the contact lens itself, and/or harming the sensitive tissues of the conjunctivae or cornea.

As pointed out in U.S. Pat. No. 3,954,965 issued May 4, 1976, hard contact lenses do not absorb appreciable amounts of water (about 0.1 to 4%) and thus, the use of effective preservatives does not create a problem in the hard contact lens field. However, users of soft contact lenses are warned not to use solutions designed for hard contact lenses for the reason that the preservative in such solutions will be absorbed and even concentrated by the soft lens resulting in possible serious damage to the soft lens/or eye; see U.S. Pat. No. Re. 29,693, issue date July 4, 1978.

The normal regimen with respect to soft lens care dictates proper cleaning and sterilization. Proteinaceous deposits tend to form and build on the lenses during wear and handling. The art suggest the use of various enzymatic cleaners such as papain or pancreatin to effectively remove such deposits. The cleaning step does not kill bacteria and other microorganisms. Therefore, a sterilization procedure which may be thermal or chemical is normally performed after the cleaning step. Thermal sterilization generally involves boiling the lens in isotonic saline solution. Chemical sterilization can be effected by soaking the lenses in solutions of chemical sterilizing agents, for example, chlorhexidine and/or thimerosal.

Accordingly it is an object of the present invention to provide an aqueous disinfectant solution for soft contact lenses which is non-toxic and nonirritating to the eye, is an effective anti-bacterial agent, and does not adsorb or penetrate into the soft contact lens.

SUMMARY OF THE INVENTION

It has now been unexpectedly discovered that hydrophilic plastic soft contact lenses may be effectively sterilized against a wide spectrum of microorganisms without deleterious effect to the lens or eye of the user with an aqueous, polymeric, anti-microbial disinfectant and/or sterilizing solution containing as an active ingredient, an effective amount of the reaction product of (a) a non-toxic, and non-irritating, anti-microbial, organosilicon quaternary ammonium salt, and (b) a water soluble, high molecular weight polymer. The molecular weight of the polymer which is chemically bound to the salt is sufficiently high so that the resultant compound cannot adsorb into the soft contact lens.

The organosilicon quaternary ammonium salt suitably constitutes about 1-25 wt %, and the water soluble polymer about 75-99 wt %, of the reaction product. In a preferred form of the invention, the organosilicon quaternary ammonium salt is present in an amount of about 5-15 wt % of the reaction product.

The molecular weight of the polymer selected will depend upon the hydrophilicity of the particular soft lens material, but generally it is at least 7,500, and preferably at least 10,000, to provide the desired property of preventing the anti-microbial composition of the invention from being absorbed into or penetrating a soft contact lens.

To provide the desired reaction product, the organosilicon quaternary ammonium salt suitably has a hydrolyzable group attached to the silicon atom which can react with the polymer. Preferably such a group is a hydrocarbonoxy silane group, such as alkoxy or acyloxy, which will provide reactive silanol groups in solution. Up to 3 such groups may be present in the molecule. A typical functional group is trimethoxy.

The water soluble, high molecular weight polymer has a reactive hydrogen therein, preferably on a pendant (side chain) group of the polymer, which can react with the hydrolyzable group of the silicon quaternary compound. Preferable polymers are polyvinylpyrrolidone, polyvinylalcohol and carboxymethyl cellulose.

The aqueous solutions useful for disinfecting soft contact lenses of the invention are characterized by being microbiologically efficacous and harmless both to the soft hydrophilic polymer soft lens and to the eye of the user.

DETAILED DESCRIPTION OF THE INVENTION

In accordance with the invention, there is provided herein an aqueous solution for disinfecting soft contact lenses which is non-toxic and non-irritating to the eye and which does not adsorb or penetrate into the soft lenses. The active ingredient of the solution is an effective amount of the reaction product of an anti-microbial, organosilicon quaternary ammonium salt having a functional group therein, and a water soluble, high molecular weight polymer reactive with said functional group.

The anti-microbial organosilicon quaternary ammonium salt compounds and their preparation are described in the literature, as for example, in U.S. Pat. Nos. 3,471,541; 3,560,385; 3,730,701; 3,817,739;

3,865,728; 4,005,028; 4,005,030; 4,394,378 and British Pat. No. 1,433,303. Particularly useful are those compounds described in U.S. Pat. Nos. 3,730,701, 3,817,739 and 4,394,378.

The essential characteristics of such compounds are anti-microbial activity, usually imparted by the presence of a long chain alkyl group on the quaternary nitrogen atom and a hydrolyzable group on the silicon atom which can be reacted with said water soluble polymer. Generally the hydrolyzable group is a hydrolyzable hydrocarbonoxy group such as alkoxy or acyloxy, for reaction with an active hydrogen of the polymer. In water solution, alkoxy and acyloxy groups are hydrolyzed to hydroxyl groups, i.e., a silanol, for reaction with the polymer.

A useful class of anti-microbial organosilicon quaternary ammonium salts are described in U.S. Pat. No. 3,730,701 and has the general formula:

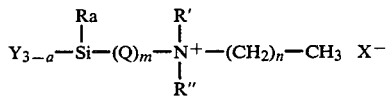

where
Y is a hydrolyzable radical, e.g. a hydrocarbonoxy group; e.g. alkoxy, or acyloxy;
R is a monovalent hydrocarbon group, e.g. lower alkyl or phenyl;
a is 0-2;
Q is a divalent hydrocarbon radical, e.g. alkylene or phenylene;
m is 1-20;
R' is alkyl $C_1$-$C_{18}$, aryl, alkaryl, or aralkyl;
R'' is lower alkyl;
n is 9-17;
X is monovalent inorganic or organic radical or group selected from halogen; triiodide; acyloxy; or $YSO_4$, where Y is a monovalent hydrocarbon, hydrogen, or $-(CH_2-)_x-COOR'''$, where X is at least 2 and R''' is a monovalent hydrocarbon group free of unsaturation.

Particularly useful compounds are those in which:
Y is alkoxy; e.g. methoxy;
R is lower alkyl; e.g. methyl;
m is 2-4; e.g. 3;
R' is lower alkyl or aralkyl; e.g. methyl or benzyl;
R'' is lower alkyl;
n is 11-17, and
X is halogen or triiodide.

Some representative compounds are the following:
Typical organosilicon quaternary ammonium salts compounds for use herein include the following:

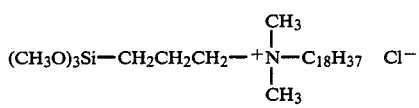

3-(trimethoxysilyl)propyloctadecyldimethyl ammonium chloride
3-(triethoxysilyl)propyloctadecyldimethyl ammonium chloride

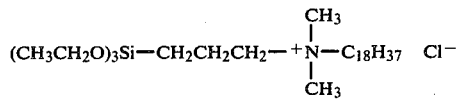

3-(methyldimethoxysilyl)propyloctadecyldimethyl ammonium chloride

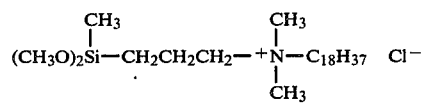

3-(phenyldimethoxysilyl)propyloctadecyldimethyl ammonium chloride

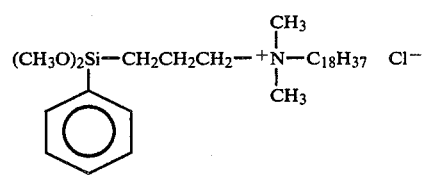

3-(dimethylmethoxysilyl)propyloctadecyldimethyl ammonium chlordie

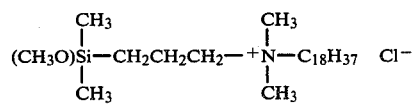

3-(diphenylmethoxysilyl)propyloctadecyldimethyl ammonium chloride

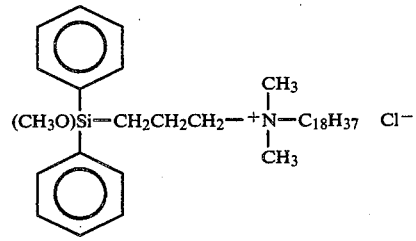

6-(methyldimethoxy)hexyloctadecyldimethyl ammonium chloride

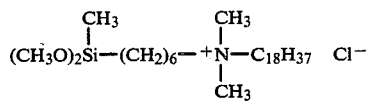

8-(methyldimethoxysilyl)octyloctadecyldimethyl ammonium chloride

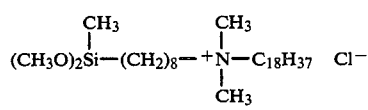

12-(methyldimethoxysilyl)dodecyloctadecyldimethyl ammonium chloride

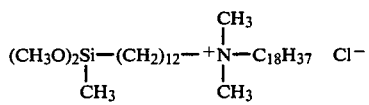

3-(methyldimethoxysilyl)propylmethyldidodecyl ammonium chloride

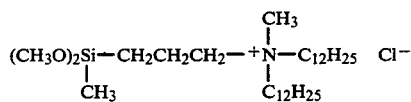

3-(methyldimethoxysilyl)propylmethyldodecylbenzyl ammonium chloride

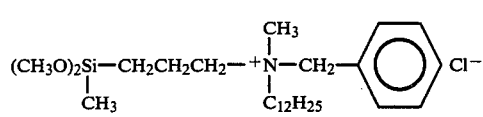

3-(methyldimethoxysilyl)propylbenzyldidodecyl ammonium chloride

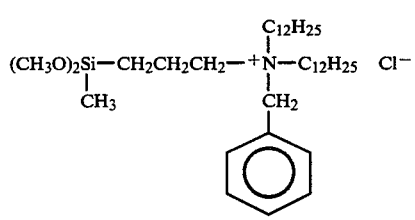

3-(trimethoxysilyl)propyloctadecyldimethyl ammonium bromide

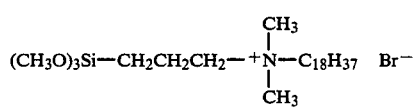

3-(trimethoxysilyl)propyloctadecyldimethyl ammonium triiodide

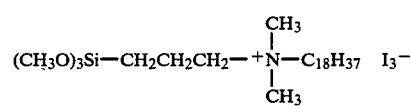

3-(trimethoxysilyl)propyloctadecyldimethyl ammonium acetate

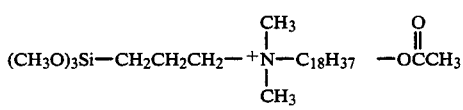

3-(trimethoxysilyl)propyloctadecyldimethyl ammonium sulfate

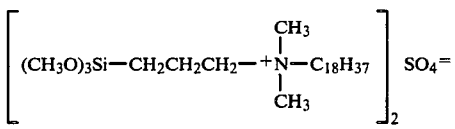

3-(methoxydimethylsilyl)propylmethyldidodecyl ammonium triiodide

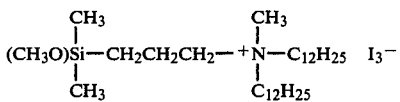

2-(trimethoxysilyl)ethyl p-benzyl dimethyloctadecyl ammonium chloride

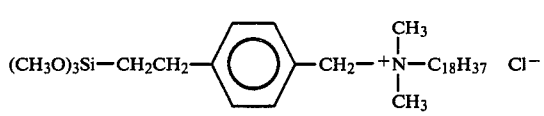

2-(trimethoxysilyl)ethyl-4-methylcyclohexyl dimethyl octadecyl ammonium chloride

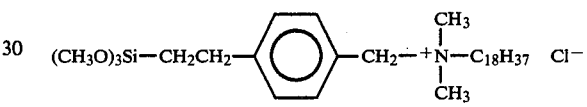

The reaction between organosilicon quaternary ammonium halide and polymer is carried out in water solution, suitably with about 1 to 25 wt % of the polymer. When the silicon component contains a trifunctional group, e.g. trialkoxy, it is preferable to use less of this component, usually about 1–15 wt %, and more preferably about 5–10 wt %. On the other hand, if only a mono- or difunctional group is present, up to 25 wt % may be used, although 5–15 wt % is preferred.

The water soluble polymers used herein are of a sufficiently high molecular weight, so that they cannot readily be adsorbed, or in many cases not absorbed at all into the hydrophilic plastic soft lens. The ability of a polymer to adsorb into a hydrophilic material depends not only on the molecular weight of the material being absorbed, but also on the degree of hydrophilicity of the polymeric soft contact lens material. For example, sparingly cross-linked polyhydroxyethyl methacrylate, which absorbs water in the neighborhood of 36 weight percent will not as readily absorb low molecular weight materials as a sparingly cross-linked vinylpyrrolidonehydroxyethyl methacrylate copolymer since the latter is much more hydrophilic and absorbs water in excess of 36 weight percent. Nevertheless, the teachings of this invention are that at a sufficiently high molecular weight depending on the specific hydrophilic plastic contact lens material used, the above anti-microbial agents chemically affixed to a water soluble polymer will not readily absorb into the soft contact lens.

Generally speaking, it was found that molecular weights of about 7,500, preferably about 10,000 or more, are suitable for this invention. There is no limit to the maximum molecular weight as long as the resulting anti-microbial agent bound to the water soluble polymer in an aqueous solution can come in contact with the surface of the hydrophilic soft contact lens material whereby microorganisms will be destroyed.

The broad generic types of water soluble polymers can be classified as the following: polyacrylamides, polymethacrylamides; polydiacetoneacrylamides; polyacrylic acids, polymethacrylic acids, polyhydroxyalkylacrylates, polyhydroxyalkylmethacrylates, water soluble cellulosics, for example, carboxymethylcellulose and hydroxymethylcellulose, polyaminoalkylacrylates, polyaminoalkylmethacrylates, polyamines, polyalkylene oxides, hydrophilic polyesters, hydrophilic polyamides; polyvinylpyrrolidone; polyvinyl alcohol; and polymers containing a sulfonic acid group, e.g. polyethylene sulfonic acid or polystyrene sulfonic acid. In addition to the above materials, combinations of graft, blend, blocked or random copolymers and terpolymers of the above, as well as other less common water soluble polymers can be utilized as long as the resulting composition is water soluble after the organosilicon quaternary ammonium halide is bound to the polymer.

Speculation of the mechanism by which these reactive anti-microbial silanes are bonded to many different types of water soluble polymers substrates suggests that the latter should have an active hydrogen atom, if a permanent chemical bond is to be formed. The hydrogen atom can be part of the polymer backbone, or on a pendant group or side chain of the polymer. In general, hydrogen atoms attached to electronegative elements like nitrogen, oxygen or sulfur can be used in this invention.

The aqueous solutions for disinfecting soft contact lenses provided herein are compatible, from pharmacological and chemical standpoints, with typical ingredients normally included in the anti-microbial or disinfectant solutions for contact lens care, and do not significantly alter the toxicity of the system. They have very low mammalian toxicity and are chemically stable, odorless and non-volatile, and exhibit a broad spectrum of anti-bacterial activity against a wide range of microorganisms which pose a danger to the eye, as exemplified by Pseudomonas aeruginosa. They are nontoxic and non-irritating to the tissues of the eye in the concentrations and frequency of use contemplated herein.

The compositions of this invention also are compatible with other ingredients usually found in ophthalmological eye care solutions. They are easily handled and applied, do not foam, and can be and are chemically stable in a wide range of pH's. However, it is preferable to apply the solutions at a pH of 7, plus or minus one unit, and in an isotonic solution, so that there will be no adverse effects to the eye from osmotic pressure due to an imbalance in the ionic strength of the solution.

In the practice of the invention, the active and non-toxic ingredient; i.e., the organosilicon quaternary ammonium halide chemically bound to a water soluble polymer, is used in an amount which is effective to impart anti-microbial or disinfecting properties to the solution against pathogens, i.e., an amount sufficient to destroy or inhibit multiplication of bacterial microorganisms such as *Staphylococcus aureus, Escherichia coli, Pseudomonas aeruginosa,* and *Aerobacter aerogenes,* while at the same time not causing irritation to the eye or damage to the lens.

Depending on the active organosilicon quaternary ammonium halide of choice and other ingredients added to the disinfecting solution, an effective amount can be as low as about 0.001 weight percent of the organosilicon quaternary ammonium salt, based on the aqueous disinfectant solution. A practical upper limit is dictated, of course, by factors which may cause eye irritation over long periods of time and/or damage to the soft contact lens. However, this invention, by virtue of the fact that the disinfectant is affixed to a water soluble, high molecular weight polymer, allows concentrated solutions of the anti-microbial material to be used without the potential of causing these problems. This advantage is quite unlike the situation when monomeric anti-microbial agents are used where adsorption and absorption are a severe problem and can cause damage to ocular tissue, and to the soft contact lens itself in many cases. An upper limit of about 0.5 weight percent of the active disinfectant material is contemplated; however, in the practice of various embodiments of the invention, a preferred upper limit is about 0.3 weight percent for general contact lens care. A practical range is from about 0.002 weight percent to about 0.1 weight percent, preferably from about 0.003 weight percent to about 0.05 weight percent.

A typical disinfectant composition useful in the practice of this invention, including aspects and embodiments thereof may contain in addition to the active ingredient buffers, stabilizers, and isotonic agents. These additional materials should be non-toxic and should not distort or otherwise damage the soft lens and they should not lower or raise the pH below 5.5 or above 8.5 since this can have an adverse effect on the occular tissue.

One aspect of the invention is concerned with a novel aqueous disinfecting solution for plastic hydrophilic soft contact lenses which desirably is substantially isotonic and which includes, in addition to the polymer bound organosilicon quaternary ammonium salt previously described, an effective amount of a water soluble salt of ethylmercurithiosalicylate, e.g., thimerosal or the corresponding potassium salt, as an additional disinfectant. The additional disinfectant is used in an amount which is non-toxic, non-irritating to the eye, and effective at concentrations documented in the literature, e.g., from about 0.001 through about 1.0 weight percent, preferably about 0.005 to 0.1 weight percent. Effective amounts of other non-toxic agents, e.g., phenylmercury salts, such as phenylmercuric nitrate and phenylmercuric acetate, suitable for use in substantially sterilizing or disinfecting soft contact lens to improve the range of organisms killed or to improve the speed of killing may also be incorporated in the novel solutions.

Over a period of time, opaque matter may gradually deposit on the soft contact lens surface which matter is not removed during the treatment with the anti-microbial solution containing the active anti-microbial ingredients. Such deposits will eventually cause the lens to lose its optical transparency and further, the lens may become increasingly more uncomfortable to wear due to irritation to the eye caused by the gradual build-up of these deposits on the lens surface. The inclusion in the novel solution of this invention of small amounts of polyvinylpyrrolidone (PVP) as part of the anti-microbial/water-soluble polymer reaction product tends to prevent the attachment of deposits to the surface of the lens.

The preparation of polyvinylpyrrolidone (PVP) is well documented in the literature; see U.S. Pat. No. 2,265,450. It can be obtained in various degrees of polymerization designated by Fichentscher K value. A preferred grade used in formulations is the pharmaceutical grade with an average molecular weight of about 40,000 and is available from GAF Corporation. Water-soluble PVP having average molecular weights of from several thousand to several hundred thousand are within the scope and spirit of the invention, e.g., from about 10,000 to about 250,000, and higher; however, commercially available PVP are, for obvious economic reasons, most suitable.

The amount of such PVP contemplated in the practice of various aspects of this invention can range from about 0.3 percent and lower, to about 10 percent and higher, desirably from 1 to about 3 percent, by weight, of the disinfectant solution. When PVP is used also as the polymer in the active ingredient, the actual percent by weight of the PVP in the final aqueous preserving solution is much higher.

The novel method of the invention involves disinfecting the soft contact lens in the above described disinfectant solution for a period of time sufficient to cause destruction or inhibition of microorganisms or othewise cause substantial sterilization of the said lens, e.g., several minutes to several hours, desirably from about 1 hour to about 6 hours, or less. Preferably, the disinfectant solution is a physiologic solution, i.e., substantially isotonic or approximately 0.9 percent saline. The foregoing method is conveniently carried out at ambient temperature or moderately elevated temperatures, e.g., upwards to about 70° C.

In various embodiments, the substantially antimicrobial or disinfectant formulation may also take the form of one or more conventional dosage forms, such as tablets suitable for use in a measured quantity of a suitable solvent such as water. The percentage composition of the solid dosage form is such that when dissolved in a specific volume of water, the resulting solution will have the percentage composition within the range contemplated in this specification. If solid dosage forms are used, the formulation may include conventional non-toxic lubricants, binders, excipients, additional active ingredients, etc., see U.S. Pat. No. 3,888,782, issued June 10, 1965, and U.S. Pat. No. 4,209,817, issued June 14, 1977, the entire disclosures of which are hereby incorporated by reference.

Over a prolonged period of time, if proteinaceous deposits should appear to accumulate on the soft contact lenses, one can affect a precleaning treatment of the lens. A simple precleaning is to generally rub the hydrated lenses between the fingers to loosen the proteinaceous deposits, then followed if desired, by soaking in physiologic saline, and then immersing and soaking in accordance with the teachings of this disclosure. Optionally, the lens may be precleaned by chemical means, e.g., soaking in a physiologic solution containing pancreatin, or by thermal means. The practice of the invention also contemplates, subsequent to the immersing and soaking the lens in the anti-microbial solution as disclosed herein, the optional step of further immersing and soaking the disinfected lens in a physiologic saline solution prior to immersion into the eye.

The soft contact lenses which are particularly suitable in the practice of various aspects of the invention, are lenses which are fabricated from gel materials such that when immersed in physiologic saline they swell and attain osmotic equilibrium therewith. Such contact lenses are illustrated by U.S. Pat. Nos. Re. 27,401; 2,976,576; 3,499,862; 3,503,942; 3,621,079; 3,639,524; 3,699,089; 3,700,761; 3,758,448; 3,772,235; 3,786,034; 3,813,447; 3,822,089; 3,937,680; 3,949,021; 3,988,274; 4,028,295; 4,056,496; 4,067,839; 4,073,577; 4,113,686; 4,123,407; 4,123,408; 4,139,513; 4,143,017; and 4,184,992. Any of the aforesaid patents disclose contact lenses comprised of polymeric hydrogels in which the polymeric network is characterized by significant amounts of polymerized mono- and polyhydroxyethyl 2-alkenoate, e.g., 2-hydroxyethyl methacrylate and dihydroxypropyl methacrylate, or polymerized N-vinyllactam e.g., N-vinylpyrrolidone, or polymerized vicinal-epoxyalkylmethacrylate, e.g., glycidyl methacrylate or other polymerized ethylenically unsaturated hydrophilic monomers. In addition to the foregoing, soft contact lenses which can be slightly hydrophilic of hydrophobic can be treated in accordance with the teachings disclosed herein. Such lenses may be characterized by significant amounts of, for example, Si or F or alkyl 2-alkenoate in their polymeric network. Such lenses may have been surface treated as by irradiation to impart desirable properties thereto. Illustrative patents in this category include U.S. Pat. Nos. 3,619,044; 3,808,178; 3,808,179; 3,940,207; 3,943,045; 3,944,347; 3,948,871; 3,950,315; 4,055,378; 4,120,570; 4,152,508; 4,168,112; 4,172,177; and 4,189,546.

Conventional hard contact lenses, e.g., poly(methylacrylate) may also be disinfected in accordance with the teachings disclosed herein. The aforesaid patents, inasmuch as they illustrate the chemistry of the contact lenses which can be disinfected by the practice of the invention are hereby incorporated by reference.

The reaction product of an anti-bacterial organosilicon quaternary ammonium salt and a water soluble, high molecular weight polymer is prepared by impregnating the water soluble polymer with a dilute aqueous solution of the silane ammonium derivative. Organic solvent systems, i.e., methanol, also can be utilized to incorporate the disinfectant onto the polymers of choice, if the silane is not readily soluble in dilute aqueous systems. The reactants then are allowed to chemically react by intimate mixing, generally at room temperature or slightly above. After the reaction is complete the mixture is filtered to remove all traces of insolubles, and any organic solvent can be removed by vacuum distillation.

For reaction, the functional group in the silane must be converted to a reactive silanol by hydrolysis for subsequent reaction with a reactive hydrogen on the polymer. Preferably the active hydrogen is present on a pendant (side chain) group of the polymer, as shown below (Sequence A). Alternatively the reaction can proceed directly (Sequence B).

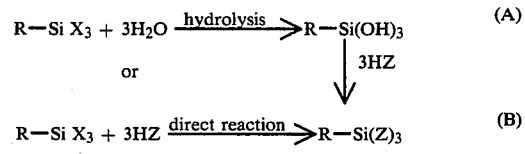

where
Z = a water soluble, high molecular weight polymer containing an active hydrogen;
X = hydrolyzable group.

The above reactions are rapid in the presence of slightly acidified water (pH 3—6).

Other methods of reacting the functional silane with active polymers may be used, as for example, dry blending, usually in a suitable liquid medium. In this technique the silane, either undiluted or mixed with a spreading solvent, is added to the polymer and thoroughly dry blended to give a uniform coating.

By this procedure, generally about 1 to about 25 weight percent of the appropriate silane ammonium derivative based on the weight of the reaction product can be incorporated. The lower range limit is a matter of microbiological efficacy, while the upper range limit is determined by several reaction variables which relate to the possible formation of a water insoluble siloxane polymer by reaction between adjacent silanol groups of the organosilicon compound. Several factors can inhibit this undesirable side-reaction including: the presence of solubilizing groups in the silane or polymer; the presence of repulsive charges; the pH of the medium; the molecular weight of the polymer; and other factors readily known by experts in the field.

The resulting disinfectant reaction product must have four major characteristics for practicing this invention. They are:
(1) the reaction product should be water soluble,
(2) the reaction product should be microbiologically efficacious,
(3) the reaction product should have a molecular weight sufficiently high so that it does not adsorb into a soft hydrophilic polymer lens, and
(4) the reaction product should be essentially chemically stable, and not break down into toxic or irritating by-products.

The optimum molecular weight of the reaction product will depend on the degree of hydrophilicity of the lens polymer. Commercial soft contact lenses, for example, have from about 30% to 80% water content once they are equilibrated. The teachings of this invention would work within and outside this range.

Hydrophilic soft contact lenses have the ability to absorb water, and will absorb a chemical solution. A solution, which otherwise might be safe in the eye, may pose a potential problem if the soft lens, upon soaking in the solution, absorbs or concentrates the chemicals of the solution in or on the lens. When this happens a wearer can be putting more than a safe concentration of chemical into the eye. Thus, an ophthalmic solution of anti-microbial agents, which are harmful to living bacteria cells, can generally be damaging to the cells of the eye if they are present in higher than normal concentrations.

Six soft contact lenses, slightly cross-linked poly(2-hydroxyethyl methacrylate), may be used in the following experiments. Three isotonic anti-microbial solutions may be employed, i.e., Solution A containing 0.01 weight percent benzalkonium chloride; Solution B containing 0.01 weight percent chlorhexidine digluconate; and Solution C containing 0.01 weight percent 3-(trimethoxysilyl) propyl-dimethyloctadecyl ammonium chloride chemically bound to polyvinyl alcohol. In all other respects the three solutions are the same. To each of the three solutions there is immersed a soft contact lens for a period of 30 days. After this period the lens is removed from each solution, washed with distilled water and inserted in a beam of an ultraviolet spectrophotometer. A clean lens previously soaked only in an isotonic solution (without any anti-microbial or preserving agent present) is used as the control or reference.

Each anti-microbial agent has a typical absorption curve, the height of which at the wavelength of maximum absorption is related to its concentration in the beam. The control lens shows no absorption at the peak wavelength. The order of decreasing uptake of anti-microbial agent in each of the immersed lenses will be as follows: benzalkonium chloride>chlorhexidine digluconate>organosilicon quaternary ammonium chloride - polyvinyl alcohol adduct.

The experiment may be repeated with the remaining three soft contact lenses. Similar results will be obtained. Data obtained with respect to Solution A (benzalkonium chloride) and Solution B (chlorhexidine gluconate) are consistent with the results reported in the text entitled Development in Industrial Microbiology, Vol 27, Chapter 18, p. 177-183 (1976) in which the authors, May Otten and John Szabocsik, conclude that "benzalkonium chloride and chlorhexidine gluconate bind strongly to the lens material" (Soflens ® Contact Lens).

In order to test the effectiveness of the polymeric germicide, lenses can be inoculated with various test organisms and then placed in a solution of 0.5% polyvinylpyrrolidone of which 10% by weight is chemically bound to 3-(trimethoxysilyl) propyl-dimethyloctadecyl ammonium chloride. Within a 6-hour period sterility will be reached for each organism. The test organisms are:

*Pseudomonas aeruginosa*
*Staphlyococcus aureus*
*Escherichia coli*
*Candida albicans*

The effectiveness of (A) 3-(trimethoxysilyl) propyl-benzylmethyloctadecyl ammonium triiodide chemically bound to carboxymethylcellulose to reduce aspergillus niger by 3 logs within 6 hours is related to the anti-microbial activity of the quaternary ammonium salt moiety of the reaction product. Accordingly, the same order of effectiveness will follow with (B) 3-(trimethoxysilyl) propyl-dimethyloctadecyl ammonium chloride chemically bound to polyhydroxyethylacrylate. Typical results expected are the following:

| Disinfecting Solution | Microorganism | Control | 6 Hours Later |
|---|---|---|---|
| (A) 0.5% CMC of which 0.05% was the disinfectant | A. niger | $10^8$ organisms/ml | $\leq 10^5$ |
| (B) 0.5% HEA of which 0.05% was the disinfectant | A. niger | $10^8$ organisms/ml | $\leq 10^5$ |

What is claimed is:
1. An aqueous solution for disinfecting soft contact lenses comprising the reaction product of an organosilicon quaternary ammonium salt of the formula:

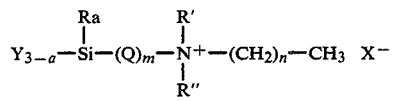

where
Y is a hydrolyzable radical, which is alkoxy, or acyloxy;
R is a monovalent hydrocarbon group, which is lower alkyl or phenyl;
a is 0-2;
Q is a divalent hydrocarbon radical, which is alkylene or phenylene;
m is 1-20;

R' is alkyl $C_1$-$C_{18}$, aryl, alkaryl, or aralkyl;
R" is lower alkyl;
n is 9-17;
X is monovalent inorganic or organic radical or group selected from the group consisting of halogen; triiodide; acyloxy; or $YSO_4$, where Y is a monovalent hydrocarbon, hydrogen, and —($CH_2$—)$_x$—COOR''', where x is at least 2 and R''' is a monovalent hydrocarbon group free of unsaturation with about 75-99 wt % of a water soluble organic polymer reactive with said hydrolyzable group and having a molecular weight sufficient to prevent the reaction product from being adsorbed into or penetrating the soft contact lens.

2. An aqueous solution for disinfecting soft contact lenses according to claim 1 wherein said polymer has a molecular weight of at least 7,500.

3. An aqueous solution for disinfecting soft contact lenses according to claim 1 wherein said reaction product comprises 0.001-0.5 wt % of said solution.

4. An aqueous solution for disinfecting soft contact lenses according to claim 1 which the organosilicon compound is present in an amount of 5-15 wt % of said reaction product.

5. An aqueous solution for disinfecting soft contact lenses according to claim 1 wherein said salt is a halide, triiodide or sulfate.

6. An aqueous solution for disinfecting soft contact lenses according to claim 1 wherein said hydrolyzable group is an alkoxy group.

7. An aqueous solution for disinfecting soft contact lenses according to claim 1 wherein said water soluble polymer is selected from the group consisting of polyacrylamides, polymethacrylamides, polydiacetoneacrylamides, polyacrylic acids, polymethacrylic acids, polyhydroxy alkacrylates, polyhydroxyalkylmethacrylates, carboxymethylcellulose, hydroxymethylcellulose, polyaminoalkylacrylates, polyaminoalkylmethacrylates, polyamines, polyalkylene oxides, hydrophilic polyesters, hydrophilic polyamides, polyvinylpyrrolidone, polyvinylalcohol, polyethylene sulfonic acid and polystyrene sulfonic acid.

8. An aqueous solution for disinfecting soft contact lenses according to claim 1 wherein Y is methoxy, R is methyl, a is 0-2, and m is 3, and X is halogen or triiodide.

9. An aqueous solution for disinfecting soft contact lenses according to claim 1 wherein said polymer is polyvinylpyrrolidone, polyvinylalcohol or carboxymethylcellulose.

10. An aqueous solution for disinfecting soft contact lenses according to claim 1 wherein said organosilicon compound is
3-(trimethoxysilyl)propyloctadecyldimethyl ammonium chloride.

11. An aqueous solution for disinfecting soft contact lenses according to claim 1 wherein said organosilicon compound is
3-(triethoxysilyl)propyloctadecyldimethyl ammonium chloride.

12. An aqueous solution for disinfecting soft contact lenses according to claim 1 wherein said organosilicon compound is
3-(methyldimethoxysilyl)propyloctadecyldimethyl ammonium chloride.

13. An aqueous solution for disinfecting soft contact lenses according to claim 1 wherein said organosilicon compound is
3-(phenyldimethoxysilyl)propyloctadecyldimethyl ammonium chloride.

14. An aqueous solution for disinfecting soft contact lenses according to claim 1 wherein said organosilicon compound is
3-(dimethylmethoxysilyl)propyloctadecyldimethyl ammonium chloride.

15. An aqueous solution for disinfecting soft contact lenses according to claim 1 wherein said organosilicon compound is
3-(diphenylmethoxysilyl)propyloctadecyldimethyl ammonium chloride.

16. An aqueous solution for disinfecting soft contact lenses according to claim 1 wherein said organosilicon compound is
6-(methyldimethoxy)hexyloctadecyldimethyl ammonium chloride.

17. An aqueous solution for disinfecting soft contact lenses according to claim 1 wherein said organosilicon compound is
8-(methyldimethoxysilyl)octyloctadecyldimethyl ammonium chloride.

18. An aqueous solution for disinfecting soft contact lenses according to claim 1 wherein said organosilicon compound is
12-(methyldimethoxysilyl)dodecyloctadecyldimethyl ammonium chloride.

19. An aqueous solution for disinfecting soft contact lenses according to claim 1 wherein said organosilicon compound is
3-(methyldimethoxysilyl)propylmethyldidodecyl ammonium chloride.

20. An aqueous solution for disinfecting soft contact lenses according to claim 1 wherein said organosilicon compound is
3-(methyldimethoxysilyl)propylmethyldodecylbenzyl ammonium chloride.

21. An aqueous solution for disinfecting soft contact lenses according to claim 1 wherein said organosilicon compound is
3-(methyldimethoxysilyl)propylbenzyldidodecyl ammonium chloride.

22. An aqueous solution for disinfecting soft contact lenses according to claim 1 wherein said organosilicon compound is
3-(trimethoxysilyl)propyloctadecyldimethyl ammonium bromide.

23. An aqueous solution for disinfecting soft contact lenses according to claim 1 wherein said organosilicon compound is
3-(trimethoxysilyl)propyloctadecyldimethyl ammonium triiodide.

24. An aqueous solution for disinfecting soft contact lenses according to claim 1 wherein said organosilicon compound is
3-(trimethoxysilyl)propyloctadecyldimethyl ammonium acetate.

25. An aqueous solution for disinfecting soft contact lenses according to claim 1 wherein said organosilicon compound is
3-(trimethoxysilyl)propyloctadecyldimethyl ammonium sulfate.

26. An aqueous solution for disinfecting soft contact lenses according to claim 1 wherein said organosilicon compound is
3-(methoxydimethylsilyl)propylmethyldidodecyl ammonium triiodide.

27. An aqueous solution for disinfecting soft contact lenses according to claim 1 wherein said organosilicon compound is 2-(trimethoxysilyl)ethyl p-benzyl dimethyloctadecyl ammonium chloride.

28. An aqueous solution for disinfecting soft contact lenses according to claim 1 wherein said organosilicon compound is 2-(trimethoxysilyl)ethyl-4-methylcyclohexyl dimethyl octadecyl ammonium chloride.

29. An aqueous solution for disinfecting soft contact lenses according to claim 1 wherein said polymer has a reactive hydrogen therein.

30. An aqueous solution for disinfecting soft contact lenses according to claim 1 wherein said polymer has a molecular weight of at least 10,000.

31. A method of disinfecting soft contact lenses which comprises applying to the lens the aqueous solution of claim 1.

32. The reaction product, which is effective as a disinfectant particularly for soft contact lenses, which results from the reaction of (i) about 1-25 wt % of an anti-microbial organosilicon quaternary ammonium salt which has the formula:

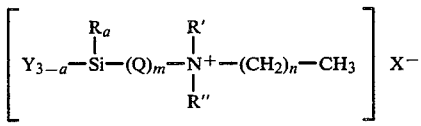

where:
Y is a hydrolyzable radical; which is alkoxy or acyloxy;
R is a monovalent hydrocarbon group which is lower alkyl or phenyl;
a is 0-2;
Q is a divalent hydrocarbon radical which is alkylene or phenylene; m is 1-20;
R' is alkyl $C_1$-$C_{18}$, aryl, alkaryl, or aralkyl;
R" is lower alkyl;
n is 9-17;
X is a monovalent inorganic or organic radical or group selected from halogen, triiodide, acyloxy or $YSO_4$; where Y is a monovalent hydrocarbon, hydrogen, or —$(CH_2)_x$—COOR''', where x is at least 2, and R''' is a monovalent hydrocarbon group free of unsaturation; with:

(ii) about 75-99 wt % of a water soluble organic polymer reactive with said hydrolyzable group and having a molecular weight sufficient to prevent the reaction product from being absorbed or penetrating a soft contact lens, wherein said polymer is selected from the group consisting of polyacrylamides, polymethacrylamides, polydiacetoneacrylamides, polyacrylic acids, polymethacrylic acids, polyhydroxy alkacrylates, polyhydroxyalkylmethacrylates, carboxymethylcellulose, hydroxymethylcellulose, polyaminoalkylacrylates, polyaminoalkylmethacrylates, polyamines, polyalkylene oxides, hydrophilic polyesters, hydrophilic polyamides, polyvinylpyrrolidone, polyvinylalchohol, polyethylene sulfonic acid and polystyrene sulfonic acid.

33. Reaction products according to claim 32 in which said polymer has a molecular weight of at least 7,500.

34. Reaction products according to claim 32 in which the organosilicon compound is present in an amount of 5-15 wt % of said reaction product.

35. Reaction products according to claim 32 wherein said salt is a halide, triiodide, sulfate or carboxylate.

36. Reaction products according to claim 32 wherein said hydrolyzable group is an alkoxy group.

37. Reaction products according to claim 32 wherein said polymer is polyvinylpyrrolidone, polyvinylalcohol or carboxymethylcellulose.

* * * * *